(12) United States Patent
Krambeck et al.

(10) Patent No.: US 11,090,154 B2
(45) Date of Patent: Aug. 17, 2021

(54) HOLDING DEVICE FOR A SUTURE RING

(71) Applicant: Berlin Heart GmbH, Berlin (DE)

(72) Inventors: Helge Krambeck, Berlin (DE); Gerhard Lauterbach, Berlin (DE); Felix Von Winterfeld, Lübeck (DE)

(73) Assignee: BERLIN HEART GMBH, Berlin (DE)

( * ) Notice: Subject to any disclaimer, the term of this patent is extended or adjusted under 35 U.S.C. 154(b) by 110 days.

(21) Appl. No.: 16/099,861

(22) PCT Filed: May 9, 2017

(86) PCT No.: PCT/EP2017/061097
§ 371 (c)(1),
(2) Date: Nov. 8, 2018

(87) PCT Pub. No.: WO2017/194562
PCT Pub. Date: Nov. 16, 2017

(65) Prior Publication Data
US 2019/0117393 A1    Apr. 25, 2019

(30) Foreign Application Priority Data

May 11, 2016 (EP) ................................ 16169259

(51) Int. Cl.
*A61F 2/24* (2006.01)
*A61M 1/10* (2006.01)
(Continued)

(52) U.S. Cl.
CPC .......... *A61F 2/2427* (2013.01); *A61F 2/2409* (2013.01); *A61M 60/857* (2021.01); *A61F 2/9517* (2020.05)

(58) Field of Classification Search
CPC .... A61F 2/2427; A61F 2/2466; A61F 2/2409; A61M 1/1008; A61B 2017/2926;
(Continued)

(56) References Cited

U.S. PATENT DOCUMENTS 4,655,218 A * 4/1987 Kulik .................... A61F 2/2427
606/205
5,188,638 A * 2/1993 Tzakis ............... A61B 17/1152
227/175.1
(Continued)

FOREIGN PATENT DOCUMENTS

| CN | 101108144 A | 1/2008 |
| CN | 103249379 A | 8/2013 |
| WO | WO 87/05489 | 9/1987 |

OTHER PUBLICATIONS

English translation of International Search Report, issued in International Application No. PCT/EP2017/061097, dated Jul. 17, 2017, pp. 1-5, European Patent Office, Rijswijk, Netherlands.

*Primary Examiner* — Darwin P Erezo
*Assistant Examiner* — Brigid K Byrd
(74) *Attorney, Agent, or Firm* — Crowell & Moring LLP

(57) ABSTRACT

A holding device for a suture ring is provided. The holding device may include a retainer in which a suture ring can be releasably fixed, in particular clamped, and a handle which is connected to the retainer and which has an actuating mechanism for fixing and/or releasing a connection between the retainer and the suture ring. By means of the holding device, a suture ring can be fixed in the retainer such that a tubular part and/or object can be pushed into the suture ring without exerting forces on the tissue to which the suture ring is connected.

7 Claims, 3 Drawing Sheets

(51) Int. Cl.
*A61M 60/857* (2021.01)
*A61F 2/95* (2013.01)

(58) Field of Classification Search
CPC .... A61B 2017/2927; A61B 2017/2932; A61B 2017/1125; A61B 17/0206; A61B 17/0293; A61B 2017/2945
See application file for complete search history.

(56) References Cited

U.S. PATENT DOCUMENTS

| | | | | |
|---|---|---|---|---|
| 5,476,510 | A | * | 12/1995 | Eberhardt .............. A61F 2/2427 606/1 |
| 5,810,878 | A | * | 9/1998 | Burel ................. A61B 17/7086 606/205 |
| 5,980,569 | A | * | 11/1999 | Scirica .................. A61F 2/2427 606/1 |
| 6,176,877 | B1 | * | 1/2001 | Buchanan ............ A61B 17/064 623/2.39 |
| 6,893,459 | B1 | | 5/2005 | Macoviak |
| 7,291,168 | B2 | | 11/2007 | Macoviak et al. |
| 8,529,580 | B1 | * | 9/2013 | Alshemari ............ A61F 11/002 606/109 |
| 9,078,750 | B2 | | 7/2015 | Carptentier et al. |
| 2002/0058994 | A1 | * | 5/2002 | Hill .................... A61B 17/0469 623/2.11 |
| 2007/0162111 | A1 | | 7/2007 | Fukamachi et al. |
| 2012/0136434 | A1 | | 5/2012 | Carpentier et al. |
| 2012/0192423 | A1 | | 8/2012 | Vesely et al. |

* cited by examiner

HOLDING DEVICE FOR A SUTURE RING

CROSS-REFERENCE TO RELATED APPLICATIONS

This application is a 371 nationalization of international patent application PCT/EP2017/061097 filed May 9, 2017, which claims priority under 35 USC § 119 to European patent application 16 169 259.5 filed May 11, 2016. The entire contents of each of the above-identified applications are hereby incorporated by reference.

TECHNICAL FIELD

The invention lies in the field of mechanics, precision mechanics, and medical technology. The invention can be used particularly advantageously in the field of surgery.

DETAILED DESCRIPTION

Figure 1:
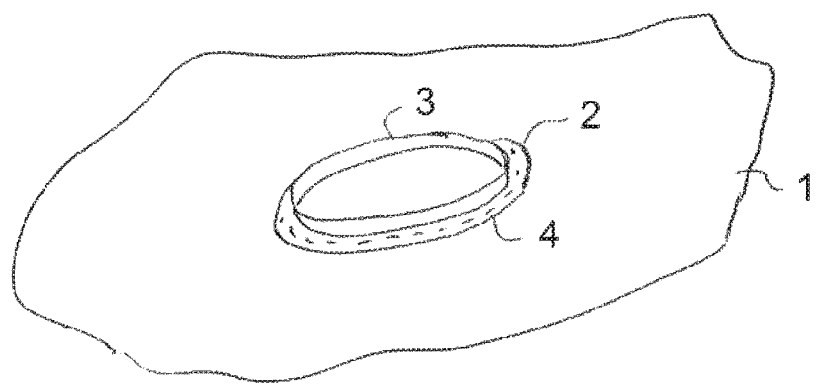
FIG. 1 schematically shows part of the surface of a heart muscle with a suture ring placed thereon in a perspective view.

In the field of surgery and implantation technology, the problem of fastening a cannula, a tube, a tube connection, or a blood pump to a blood vessel or directly to the heart of a patient is often encountered. Here, the fastening should be as gentle as possible on the tissue, reliable, and as leak-proof as possible. What are known as suture rings are usually used for this purpose, which on the one hand can be securely sewn to the tissue of the vessel or the heart and on the other hand offer a connection for a cannula, a tube or a tube connection. For this purpose, a suture ring of this kind offers a part that can be sewn, which for example can be formed from a woven fabric, and a fixed ring for insertion of a counter piece. Once the suture ring has been sewn to the tissue, the myocardium within the suture ring is usually cut out using a surgical tool (ring cutter or cutting tool) so as to create access to the corresponding ventricle or also atrium. A cannula or a tube is then introduced or inserted into this access point. The tube or the cannula can be part of a blood pump directly.

The part that is inserted into the suture ring is usually formed with a custom fit, such that an insertion connection that is as firm and leak-proof as possible is created. However, when making the connection between the suture ring and the part that is to be inserted, forces are applied whilst the connection or the insertion is being established, said forces being transferred to the tissue by the suture ring. For example, a seal in the form of an elastomer O-ring can be provided between the parts to be connected, which seal increases the insertion forces. In addition, a locking element can be provided, which is inserted or pushed in once the connection has been established so as to prevent a subsequent removal of the inserted part.

In particular, in the case of a weakened heart, the wall of the heart muscle can become thin and weak. There is thus a risk that the heart will become deformed at the connection point and that the tissue might tear, which can lead to a very high blood loss for the patient and to the need for further treatment.

The object of the present invention is therefore to create a holding device for a suture ring, which allows the connection between the suture ring and a part that is to be inserted thereinto, in particular a tube, tube connection or a cannula, to be established in a gentle manner.

Accordingly, the invention relates to a holding device for a suture ring with a retainer in which a suture ring can be releasably fixed, in particular clamped, and with a handle which is connected to the retainer and which has an actuating mechanism for fixing and/or releasing the connection between the retainer and the suture ring.

By means of the actuation device, the suture ring can be securely fixed in the retainer of the holding device. In this way, the suture ring can then be held comfortably by means of the holding device whilst a tubular part for example is pushed in, such that forces acting as said tubular part is pushed in onto the suture ring can be taken up by means of the holding device and therefore do not act on the tissue to which the suture ring is sewn.

Once the object has been pushed into the suture ring, the connection between the holding device and the suture ring can be released again by actuating the actuating device and the handle, and the suture ring can be let go of in this way.

One possible embodiment of the holding device can provide that the retainer has a clamping device with clamping elements movable relative to one another.

Here, it can be provided that the retainer is formed in the manner of a pair of tongs having two clamping jaws.

So as to be able to bring the suture ring into a defined position, it can be provided that a suture ring can be fixed, in particular clamped, in a defined position relative to the retainer. On the one hand, the suture ring thus can be brought easily into a defined position by means of the holding device, and on the other hand, the position of the suture ring relative to the holding device also can be defined reliably and reproducibly.

The holding device for this purpose can comprise recesses on the clamping jaws, into which the suture ring fits. Particular shaped portions of the clamping jaws can also be provided, which fit together with protrusions or recesses of the suture ring, which are shaped in a complementary manner accordingly, such that the relative position between the suture ring and the holding device is defined unequivocally and reproducibly by means of a mechanical coding.

It can also be provided that the handle comprises two lever arms, which are connected one to each of the clamping jaws and can be pivoted relative to one another. In this way, the lever arms can be easily actuated by a hand of a surgeon or an assistant, in such a way that the suture ring is clamped and securely held in the holding device.

It can also be provided that each of the lever arms is connected to a shaft, which shafts are rotated in the event of a pivoting motion of the lever arms relative to one another, wherein each of the shafts is connected to one of the clamping jaws.

In addition, it can be provided here that a common pivot plane of the lever arms is offset in parallel relative to a common pivot plane of the clamping jaws. By means of the offset of the pivot planes of the lever arms on the one hand and of the clamping jaws on the other hand, a suture ring can also be held in place without major problems at points that are difficult to access, without the lever arms of the handle having to be actuated at a point close to the suture ring. Rather, the handle with its lever arms can be offset relative to the clamping jaws perpendicular to the pivot plane of the clamping jaws, for example by a few centimeters to a few tens of centimeters. During the operation, space in the vicinity of the suture ring is thus free, or rather the opening in the patient's body can be reduced.

It can additionally be provided that the holding device comprises a guide for an object that is to be introduced into a suture ring, which guide guides a movement of the object in the direction of the position assumed by a suture ring fixed in the holding device. By means of the guide, the insertion of an object, in particular a tubular part, into the opening of the suture ring is facilitated. On the one hand, it is made easier to reach the opening of the suture ring with the object that is to be introduced, and on the other hand the occurring forces and movements and, thus, also the negative influence on the tissue to which the suture ring is connected can be limited.

It can additionally be provided that the holding device comprises a connecting device for establishing a connection between an object and a suture ring, which connecting device on the one hand is supported on part of the holding device and on the other hand is designed to displace the object in the direction of a position assumed by a suture ring fixed in the holding device.

If, when the object/tubular part is introduced into the opening of the suture ring, the connecting device is on the one hand connected to the holding device and on the other hand is supported on the object that is to be introduced, a force can be exerted onto the object, which force can be taken up directly in the connecting device or at the holding device, such that the suture ring is supported there and no force is exerted onto the tissue to which the suture ring is connected.

Here, it can be provided that the connecting device can be driven by a lever mounted on the holding device. The force on the object can be increased or reduced by means of a lever device, such that higher forces necessary to push the object into the suture ring and to overcome the frictional forces can also be generated in a simple and safe manner. At the same time, by means of the lever mechanism, the path traveled by the object when pressed into the suture ring can be reliably limited, or the end position of the object in the suture ring can be defined.

The holding device can be designed for this purpose such that a part of the connecting device can be positioned in a first position in such a way that the free arrangement of an object in front of the suture ring is made possible, and in such a way that the part can be pivoted into a second position behind the object or behind a protrusion of the object, in such a way that it is possible, by means of the lever, to push the object into the suture ring.

The holding device is expediently also designed such that the drive movement of the lever in a third position is limited in such a way that an object in the suture ring that is to be connected reaches its end position with the end of the drive movement of the lever. Once the object has reached its end position in the suture ring, the holding device can be released and removed from the suture ring. To facilitate pushing of the object into the suture ring, markings can also be provided which show that an end position of the con-necting device and of the object to be pushed in has been reached. To this end, a press ram for a press plate of the connecting device, in its end position, can finish flush with the edge of a guide opening in which it is guided.

In addition to a holding device of the above-described and explained type, the invention also relates to a method for establishing a connection between a suture ring and an object in the form of a tubular part that can be pushed into the suture ring, wherein the suture ring is held by means of a holding device, and wherein the tubular part is introduced into the holding device and is pushed into the suture ring by actuation of a lever of a connecting device.

Figure 3:
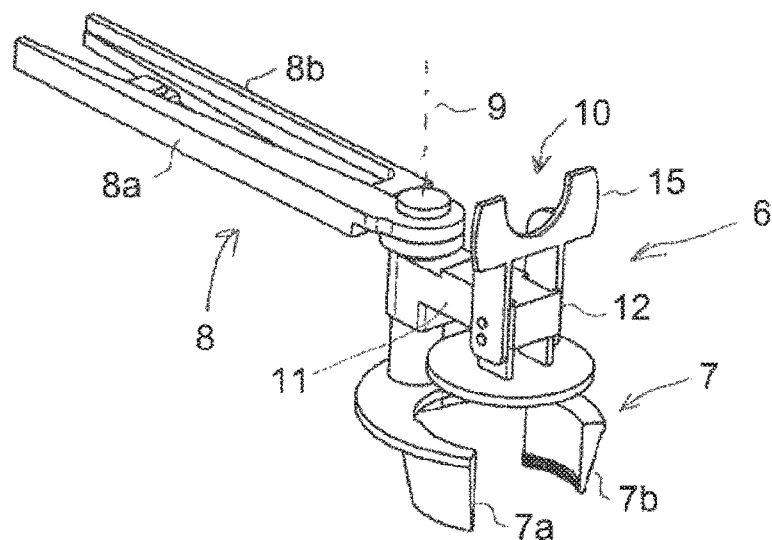
FIG. 3 shows a holding device in a perspective view.
Figure 4:
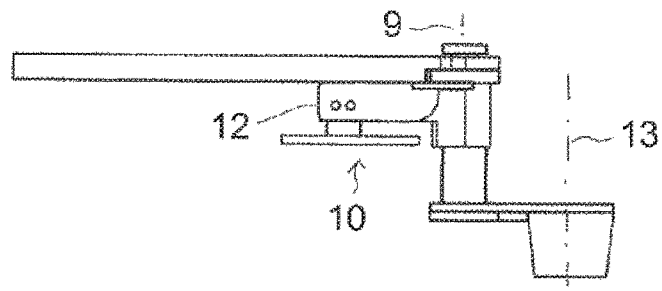
FIG. 4 shows a holding device in a side view with a connecting device in a first position.
Figure 5:
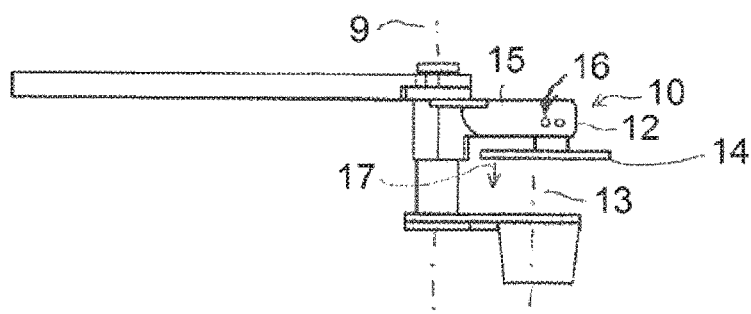
FIG. 5 shows a holding device in a side view with a connecting device in a second position.
Figure 6:
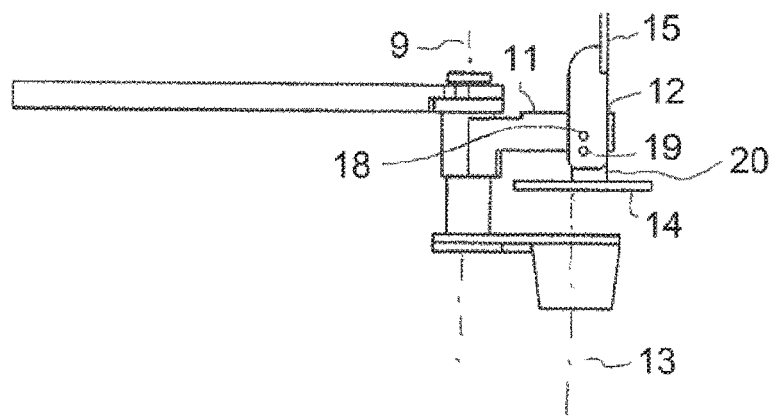
FIG. 6 shows a holding device with a connecting device in a third position.
Figure 7:
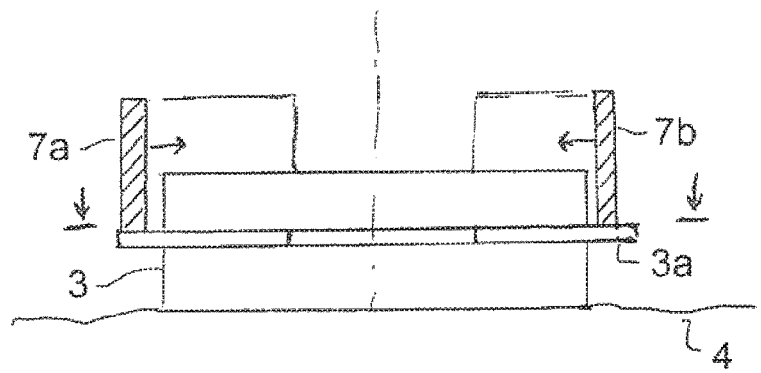
FIG. 7 shows clamping jaws of a holding device in cooperation with a suture ring.
Figure 8:
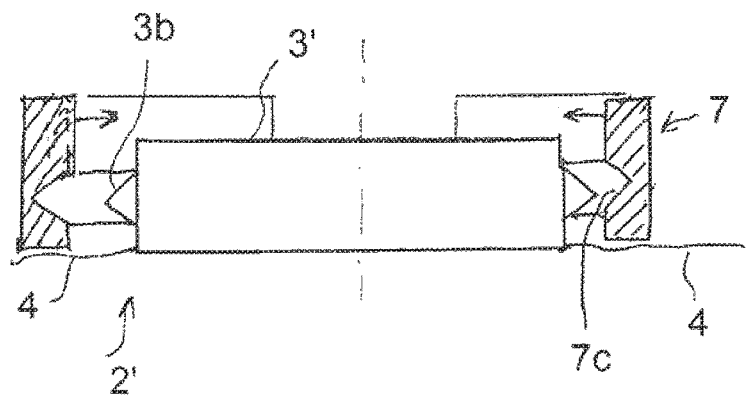
FIG. 8 shows a further embodiment of clamping jaws in cooperation with a suture ring.

The invention will be presented hereinafter on the basis of exemplary embodiments in figures of a drawing and will then be explained. In the figures FIG. 1 schematically shows part of the surface of a heart muscle with suture ring placed thereon in a perspective view, FIG. 2 shows a suture ring with a tubular object to be pushed into the suture ring, FIG. 3 shows a holding device in a perspective view, FIG. 4 shows a holding device in a side view with a connecting device in a first position, FIG. 5 shows a holding device in a side view with a connecting device in a second position, FIG. 6 shows a holding device with a connecting device in a third position, FIG. 7 shows clamping jaws of the holding device in cooperation with a suture ring, and FIG. 8 shows a further embodiment of clamping jaws in cooperation with a suture ring.

FIG. 1, in a perspective illustration, shows a part of the surface of a patient's heart 1, on which a suture ring 2 is placed. A suture ring of this kind consists of a solid, often metal ring part 3, which is firmly connected to a flange part 4, which can be sewn. The flange part, which can be sewn, can be embodied in a fabric-like or film-like manner, such that it can be sewn by a surgeon to the tissue to which the suture ring is to be fastened during the implantation process.

Figure 2:
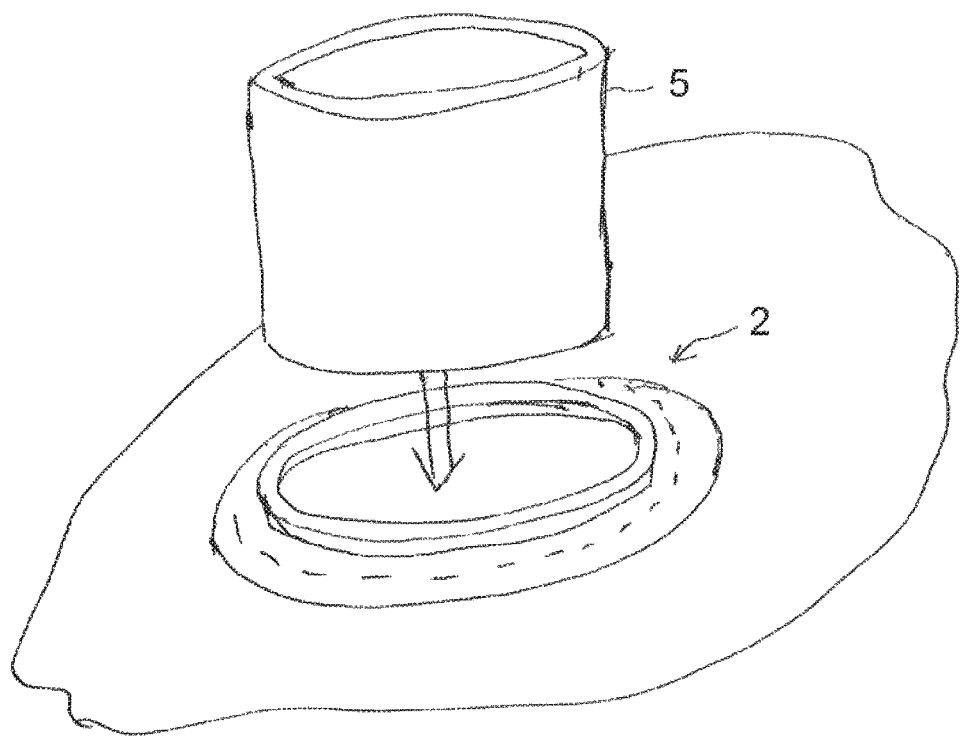
FIG. 2 shows a suture ring with a tubular object to be pushed into a suture ring.

FIG. 2 shows the suture ring 2, already shown in FIG. 1, in cooperation with a tubular part or object 5 that is to be inserted into the suture ring 2.

Once the suture ring 2 has been sewn in place, within the suture ring a circular portion is usually cut out or pressed out from the tissue, that is to say for example of the heart wall, onto which the suture ring has been placed, so as to create an opening in the heart wall. A tubular element/object 5 is intended to be coupled to this opening. For this purpose, the tubular element/object 5 is pushed into the suture ring. The dimensions of the suture ring and of the tubular part/object 5 are adapted to one another in such a way that the tubular part/object 5 sits securely and in a leak-proof manner in the suture ring. For this purpose, sealing elements can also be provided either in the tubular part/object 5 or in the suture ring 2.

A leak-proof connection of this kind means that, as the tubular part/object 5 is pushed into the suture ring 2, forces occur that are not insignificant. These forces can be taken up at least in part in that a surgeon, during the operation, firmly holds the suture ring 2 as the tubular part/object 5 is pushed in. An approach of this kind, however, is not always satisfactory in all situations. This problem is remedied by means of the holding device according to the invention.

The tubular part/object 5 is shown here merely by way of example and can be a pipe connection, to which a pump (not shown in greater detail) or a pump itself with a pipe connection fastened thereto or a rigid cannula or part of a cannula is fastened. Other objects which have to be pushed into a suture ring 2 are also conceivable, instead of the tubular part 5.

FIG. 3 shows a holding device 6 in a perspective illustration. A retainer 7 with two clamping jaws 7a, 7b is shown, between which a suture ring 2 can be clamped.

The two clamping jaws 7a, 7b are pivotable relative to one another about a common axis 9, such that a suture ring can be clamped between them in a tong-like manner. The two clamping jaws 7a, 7b are connected to two coaxial shafts movable one inside the other, which extend along the axis 9 in the holding device.

The individual shafts are connected to the two levers 8a, 8b of the handle 8 in such a way that, when the handle 8 is pressed together, this at the same time causes the two clamping jaws 7a, 7b to be pressed together. The pivot planes of the levers 8a, 8b on the one hand and of the clamping jaws 7a, 7b on the other hand are offset relative to one another along the axis 9. The holding device thus also can be inserted easily at inaccessible points, such that on the one hand a suture ring can be grasped by the clamping jaws 7a, 7b, but on the other hand the handle 8 is easily accessible and can be actuated at a point distant therefrom.

The holding device 6, apart from the actuating device/the handle 8 and the retainer 7, also comprises a connecting device 10. This is mounted rotatably about the axis 9 of the holding device and comprises a rotary arm 11, which carries a pressing device 12. The rotary arm is fixed in the axial direction of the axis 9 and allows only a rotation of the pressing device 12 about the axis 9. The pressing device is supported on the other parts of the holding device by means of the rotary arm 11.

FIG. 4 shows a first position of the connecting device 10, in which the rotary arm 11 and the pressing device 12 are pivoted away from the clamping jaws 7a, 7b. In FIG. 4 an axis 13 is shown, which represents the central axis of an object to be grasped by the clamping jaws 7a, 7b, i.e. at the time of use the central axis of a suture ring that is fixed by the clamping jaws 7a, 7b. The first position of the connecting device is selected in such a way that the axis 13 is free, such that the space for introducing a tubular part/object 5 is free.

FIG. 5 shows the connecting device 10 in a second position, in which the rotary arm 11 is pivoted in the direction of the axis 13. The connecting device 10 and the pressing device 12 now lie above the tubular part 5 to be pressed into the suture ring. The pressing device 12 comprises a press plate 14, an actuation lever 15, and a lever mechanism 16, which converts a pivoting of the actuation lever 15 into a downward movement of the press plate 14 in the direction of the arrow 17.

The lever mechanism for example comprises a shaft 18 by means of which the actuation lever 15 is mounted on the rotary arm 11, and an actuating splint 19, which is movable in a slotted guide of a press ram 20, to which the press plate 14 is fastened. If the actuation lever 15 is pivoted upwardly into the vertical position as far as a stop (not shown), the splint 19 thus actuates the press ram 20 in such a way that said press ram is driven downwardly in the direction of the arrow 17 until in its end position. The press ram 20 is guided here in a guide within the rotary arm 11 in such a way that it cannot deviate laterally from the axis 13, and instead can move merely in the direction of the axis 13.

If the actuating lever 15 is moved into the position shown in FIGS. 3 and 6, the connecting device is brought into a third position, in which the part/object to be pushed into the suture ring is displaced precisely to such an extent that the connection to the suture ring is reliably established. The forces acting during this pushing-in movement act here exclusively between the retainer 7 and the connecting device within the holding device, such that in the ideal case no forces at all act on the tissue to which the suture ring 2 is connected.

The length of the feed movement of the press ram 20 of the connecting device is based on the size of the tubular part/object 5 to be pushed into the suture ring 2.

In order to bring the suture ring into a defined position relative to the holding device for the functioning of the holding device, it is provided that the suture ring is clamped in a defined position in the retainer 7.

FIG. 7 shows, in an exemplary manner, the clamping jaws 7a, 7b, which are placed against a flange 3a of the ring part 3 of the suture ring 2 before the suture ring is clamped. A relative position between the holding device and the suture ring is thus defined.

FIG. 8 shows, in a further exemplary embodiment, a suture ring 2' with a ring part 3', which has a circumferential rib 3b of triangular cross-section, which engages in a complementary groove 7c in the clamping jaws of the retainer 7 when the clamping jaws close around the suture ring 2'. The contour of the circumferential rib 3b is selected such that this is centred in the groove 7c and the relative position between the holding device and the suture ring 2' is thus defined.

To clarify the use of and to hereby provide notice to the public, the phrases "at least one of <A>, <B>, . . . and <N>" or "at least one of <A>, <B>, . . . <N>, or combinations thereof" or "<A>, <B>, . . . and/or <N>" are defined by the Applicant in the broadest sense, superseding any other implied definitions hereinbefore or hereinafter unless expressly asserted by the Applicant to the contrary, to mean one or more elements selected from the group comprising A, B, . . . and N. In other words, the phrases mean any combination of one or more of the elements A, B, . . . or N including any one element alone or the one element in combination with one or more of the other elements which may also include, in combination, additional elements not listed. Unless otherwise indicated or the context suggests otherwise, as used herein, "a" or "an" means "at least one" or "one or more."

The invention claimed is:

1. A holding device for a suture ring, the holding device comprising:
    a retainer in which the suture ring can be releasably fixed; and
    a handle which is connected to the retainer and which has an actuating mechanism for fixing and/or releasing a connection between the retainer and the suture ring, wherein the retainer comprises a clamping device including a pair of tongs having two clamping jaws configured to move relative to one another and clamp the suture ring, at an outer circumference of the suture ring, between the two clamping jaws in a defined position relative to the retainer, wherein each of the clamping jaws comprises a curved gripping surface for clamping a curved outer circumference of the suture ring,
    wherein the handle comprises two lever arms, which are connected one to each of the clamping jaws and can be pivoted relative to one another,
    wherein each of the lever arms is connected to a shaft, which shafts are rotated in the event of a pivoting motion of the lever arms relative to one another, wherein each of the shafts is connected to a respective one of the clamping jaws, wherein a common pivot plane of the lever arms is offset in parallel relative to a common pivot plane of the clamping jaws, the curved gripping surface of the clamping jaws extending in parallel with the pivot plane of the clamping jaws.

2. The holding device of claim 1 further comprising a guide for an object that is to be introduced into the suture ring, wherein the guide guides a movement of the object in the direction of the position assumed by the suture ring fixed in the holding device.

3. The holding device of claim 1 further comprising a connecting device for establishing a connection between an object and the suture ring, wherein the connecting device is supported on a part of the holding device and is configured to displace the object in the direction of a position assumed by the suture ring fixed in the holding device.

4. The holding device of claim 3, wherein the connecting device can be driven by a lever mounted on the holding device.

5. The holding device of claim 4, wherein a part of the connecting device can be positioned in a first position in such a way that a space for introducing and arranging an object between the suture ring and a user is free, and in that the part can be pivoted into a second position behind the object, as seen in a direction from the suture ring being held, or behind a protrusion of the object, as seen in the direction from the suture ring being held, in such a way that it is possible, by means of the lever, to push the object into the suture ring.

6. The holding device of claim 4, wherein the drive movement of the lever in a third position is limited in such a way that an object in the suture ring that is to be connected to the suture ring reaches its end position with the end of the drive movement of the lever.

7. A method for establishing a connection between a suture ring and an object having a tubular part that can be inserted into the suture ring, the method comprising:

holding the suture ring with a holding device, the holding device comprising a retainer in which the suture ring can be releasably fixed, and a handle which is connected to the retainer and which has an actuating mechanism for fixing and/or releasing a connection between the retainer and the suture ring, wherein the retainer comprises a clamping device including a pair of tongs having two clamping jaws configured to move relative to one another and clamp the suture ring, at an outer circumference of the suture ring, between the two clamping jaws in a defined position relative to the retainer, wherein the handle comprises two lever arms, which are connected one to each of the clamping jaws and can be pivoted relative to one another, wherein each of the lever arms is connected to a shaft, which shafts are rotated in the event of a pivoting motion of the lever arms relative to one another, wherein each of the shafts is connected to a respective one of the clamping jaws, wherein a common pivot plane of the lever arms is offset in parallel relative to a common pivot plane of the clamping jaws wherein each of the clamping jaws comprises a curved gripping surface for clamping a curved outer circumference of the suture ring, the curved gripping surface of the clamping jaws extending in parallel with the pivot plane of the clamping jaws;

introducing the tubular part into the holding device;

clamping the suture ring between the two clamping jaws in the defined position relative to the retainer; and pushing the tubular part into the suture ring by actuation of a lever of a connecting device.

\* \* \* \* \*